(12) United States Patent
Ricketts et al.

(10) Patent No.: US 12,115,306 B2
(45) Date of Patent: Oct. 15, 2024

(54) AEROSOL-GENERATING DEVICE HAVING A CHAMBER FOR RECEIVING A REMOVALBE LIQUID CONTAINER

(71) Applicant: Philip Morris Products S.A., Neuchatel (CH)

(72) Inventors: Nikolaus Martin Ernest Wilhelm Ricketts, Neuchatel (CH); Philippe Slama, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 891 days.

(21) Appl. No.: 17/048,388

(22) PCT Filed: Apr. 17, 2019

(86) PCT No.: PCT/EP2019/060023
§ 371 (c)(1),
(2) Date: Oct. 16, 2020

(87) PCT Pub. No.: WO2019/202048
PCT Pub. Date: Oct. 24, 2019

(65) Prior Publication Data
US 2021/0145050 A1     May 20, 2021

(30) Foreign Application Priority Data
Apr. 17, 2018   (EP) .................................... 18167841

(51) Int. Cl.
*A61M 15/06*     (2006.01)
*A24F 40/10*     (2020.01)
*A24F 40/40*     (2020.01)

(52) U.S. Cl.
CPC ............. *A61M 15/06* (2013.01); *A24F 40/40* (2020.01); *A24F 40/10* (2020.01)

(58) Field of Classification Search
CPC .......... A24F 40/40; A24F 40/10; A61M 15/06
See application file for complete search history.

(56) References Cited

U.S. PATENT DOCUMENTS

| 8,881,737 B2 | 11/2014 | Collett et al. |
| D805,686 S | 12/2017 | Perez |
| (Continued) | | |

FOREIGN PATENT DOCUMENTS

| CN | 2760984 Y | 3/2006 |
| CN | 204560971 U | 8/2015 |
| (Continued) | | |

OTHER PUBLICATIONS

Japanese Office Action issued Feb. 15, 2023 in Japanese Application 2020-555221, (with English translation), 10 pages.

(Continued)

*Primary Examiner* — Hae Moon Hyeon
(74) *Attorney, Agent, or Firm* — Oblon, McClelland, Maier & Neustadt, L.L.P.

(57) ABSTRACT

An aerosol-generating device is provided, including: a housing defining a mouthpiece end, a distal end, a sidewall between the mouthpiece end and the distal end, and a chamber within the housing, the chamber being configured to receive a liquid container, the housing including a retainer configured to retain the liquid container within the housing, the retainer including a magnetic retention mechanism; and a power source disposed within the housing, the sidewall of the housing defining an insertion window through which the liquid container is positionable inside the chamber. An aerosol-generating system and a liquid container are also provided.

12 Claims, 4 Drawing Sheets

(56) References Cited

U.S. PATENT DOCUMENTS

| | | | |
|---|---|---|---|
| D805,687 S | 12/2017 | Perez | |
| 10,010,687 B2* | 7/2018 | Von Schuckmann | A61M 15/0026 |
| 10,015,990 B2* | 7/2018 | Mironov | A61M 11/042 |
| 10,328,443 B2* | 6/2019 | Ricketts | B05B 11/0054 |
| 10,874,142 B2* | 12/2020 | Mironov | A61M 15/06 |
| 10,925,317 B2* | 2/2021 | Smith | A24F 40/30 |
| 11,278,688 B2* | 3/2022 | Azevedo | A61K 9/0078 |
| 11,311,047 B2* | 4/2022 | Reevell | A24F 40/30 |
| 11,433,191 B2* | 9/2022 | Fallon | A24F 40/42 |
| 11,445,747 B2* | 9/2022 | Rojo-Calderon | A24F 7/00 |
| 2005/0016550 A1 | 1/2005 | Katase | |
| 2015/0053217 A1 | 2/2015 | Steingraber et al. | |
| 2015/0090253 A1* | 4/2015 | Farrow | A61M 15/0003 128/200.14 |
| 2015/0216233 A1 | 8/2015 | Sears et al. | |
| 2015/0367366 A1* | 12/2015 | Edwards | A23G 1/50 239/302 |
| 2016/0150828 A1* | 6/2016 | Goldstein | H05B 6/36 392/387 |
| 2016/0345629 A1 | 12/2016 | Mironov | |
| 2017/0064999 A1 | 3/2017 | Perez | |
| 2017/0150755 A1 | 6/2017 | Batista | |
| 2017/0172211 A1* | 6/2017 | Batista | A24F 40/485 |
| 2017/0202265 A1* | 7/2017 | Hawes | A61M 11/041 |
| 2017/0238617 A1 | 8/2017 | Scatterday | |
| 2017/0245554 A1 | 8/2017 | Perez | |
| 2017/0280773 A1 | 10/2017 | Force | |
| 2017/0334605 A1 | 11/2017 | Murphy et al. | |
| 2018/0084836 A1 | 3/2018 | Perez | |
| 2019/0098930 A1 | 4/2019 | Fallon et al. | |
| 2020/0022416 A1* | 1/2020 | Alarcon | A24F 40/57 |
| 2020/0281268 A1* | 9/2020 | Wright | A24F 15/01 |
| 2021/0244092 A1* | 8/2021 | Weigensberg | H05B 3/10 |

FOREIGN PATENT DOCUMENTS

| | | |
|---|---|---|
| CN | 107105767 A | 8/2017 |
| EP | 2 875 740 A2 | 5/2015 |
| JP | 2005-34021 A | 2/2005 |
| KR | 10-2018-0008332 A | 1/2018 |
| RU | 2 588 456 C2 | 6/2017 |
| WO | WO 2014/150826 A1 | 9/2014 |
| WO | WO 2015/117700 A1 | 8/2015 |
| WO | WO 2016/054580 A1 | 4/2016 |
| WO | WO 2016/075028 A1 | 5/2016 |
| WO | WO 2016/174179 A1 | 11/2016 |
| WO | WO 2017/167932 A1 | 10/2017 |
| WO | WO 2018/002994 A | 1/2018 |
| WO | WO 2018/016805 A1 | 1/2018 |
| WO | WO 2018/050610 A1 | 3/2018 |
| WO | WO 2018/050612 A1 | 3/2018 |
| WO | WO 2019/081898 A1 | 5/2019 |

OTHER PUBLICATIONS

Extended European Search Report issued Sep. 17, 2018 in European Patent Application No. 18167841.8, 9 pages.

International Search Report and Written Opinion issued on Jun. 21, 2019 in PCT/EP2019/060023 filed on Apr. 17, 2019.

Office Action issued Aug. 25, 2023, in corresponding European Patent Application No. 19 717 498.0, citing documents 15 and 16 therein, 6 pages.

Combined Chinese Office Action and Search Report issued Aug. 3, 2023 in Chinese Patent Application No. 201980021970.0 (with English Translation), 13 pages.

Combined Russian Office Action and Search Report issued Aug. 4, 2022, in corresponding Russian Patent Application No. 2020133962 (with English Translation), 17 pages.

European Office Action issued Nov. 3, 2022 in European Patent Application No. 19717498.0, 6 pages.

Korean Office Action issued on Mar. 18, 2024 in Korean Patent Application No. 10-2020-7032574 (with unedited computer-generated English translation), 7 pages.

Japanese Office Action mailed Aug. 20, 2024 issued in Japanese Patent Application No. 2020-555221, with English Translation, total 12 pages.

* cited by examiner

AEROSOL-GENERATING DEVICE HAVING A CHAMBER FOR RECEIVING A REMOVALBE LIQUID CONTAINER

CROSS-REFERENCE TO RELATED APPLICATIONS

This application is a U.S. national stage application of PCT/EP2019/060023, filed on Apr. 17, 2019, which is based upon and claims the benefit of priority under 35 U.S.C. § 119 to European patent application no. 18167841.8, filed Apr. 17, 2018, the entire contents of each of which are incorporated herein by reference.

TECHNICAL FIELD

The present invention relates to an aerosol-generating system comprising an aerosol-generating device and a container containing an aerosol-forming substrate.

DESCRIPTION OF THE RELATED ART

Aerosol-generating systems, such as e-cigarettes, that generate an aerosol for user inhalation have become increasingly popular. These aerosol-generating systems are typically handheld systems that comprise a reusable component, comprising a power source and control circuitry, and a consumable component containing an aerosol-forming substrate from the aerosol is generated. The system also includes an aerosol generating element, such as a heater, which is powered by the power source but may be positioned in the reusable component or in the consumable component.

It is desirable for the consumable component to be a simple and inexpensive as possible. It is also desirable for the consumable component to be easily attached to and removed from the reusable component.

Some aerosol-generating systems comprise a main device, a cartridge, and a mouthpiece. The device has a housing accommodating a heater and electrical components such as a power source and a control circuitry. The housing defines a cavity where the cartridge can be positioned to be electrically connected to the power source. The mouthpiece, which is positioned downstream from the cavity, is in threaded engagement with the housing and covers the cavity of the main device.

The cartridge is removably installed within the cavity, so that the cartridge may be replaced with a new cartridge when required. In order to replace the cartridge, the mouthpiece is required to be disassembled. Thereafter, the cartridge can be accessed and replaced. However, it may be cumbersome and unappealing for users to frequently disassemble the mouthpiece from the main device, in order to replace the cartridge from the cavity of the main device, in particular with single use cartridges designed to contain aerosol-forming substrate sufficient for only a single user experience.

In other aerosol-generating systems, the cartridge is provided with a mouthpiece, which is screwed or otherwise removably fastened to the main device. However, including the mouthpiece in the cartridge leads to more material consumption which is both expensive and less environmentally friendly.

It is the aim of the present invention to provide an aerosol-generating system in which the cartridge can be replaced more conveniently, and which also may allow a disposable cartridge to be as simple as possible, without excessive elements.

SUMMARY

According to a first aspect of the present invention there is provided an aerosol-generating device, comprising a housing, the housing defining a mouthpiece end, a distal end, a sidewall between the mouthpiece end and the distal end, and a chamber within the housing, the chamber being adapted to receive a liquid container, wherein the housing comprises retention means adapted to retain the liquid container within the housing, the retention means comprising a retention lever; and a power source positioned within the housing; wherein the sidewall of the housing defines an insertion window through which the liquid container can be positioned inside the chamber.

The aerosol-generating device may comprise a housing, the housing defining a mouthpiece end, a distal end, a sidewall between the mouthpiece end and the distal end, and a chamber within the housing, the chamber being adapted to receive a liquid container; and a power source positioned within the housing; wherein the sidewall of the housing defines an insertion window through which the liquid container can be positioned inside the chamber.

According to a second aspect of the present invention there is provided an aerosol-generating system. The system comprises an aerosol-generating device comprising a housing, the housing defining a mouthpiece end, a distal end, a sidewall between the mouthpiece end and the distal end, and a chamber within the housing. The system further comprises a power source positioned within the housing; and a liquid container, the liquid container comprising a liquid aerosol-forming substrate. The sidewall of the housing defines an insertion window through which the cartridge can be positioned inside the chamber.

BRIEF DESCRIPTION OF THE DRAWINGS

Specific embodiments of the present invention will now be described, by way of example only, with reference to the accompanying drawings in which.

DETAILED DESCRIPTION

With the features of the first or the second aspect of the present invention, there is no need to unscrew the device or take the device apart by removing a mouthpiece or a bottom part of the housing. The liquid container can therefore be accessed or replaced in a simplified manner. The liquid container itself can be simplified, having no additional features such as an integrated mouthpiece, and thus can be made cheaper.

According to a third aspect of the present invention, there is provided a liquid container comprising a liquid aerosol-forming substrate, the liquid container being adapted to be used with an aerosol-generating device of the first aspect of the invention.

Below, advantageous features of one or more embodiments are described. It is clear to the skilled person that the embodiments described below may be combined together.

Once the system is assembled, the liquid container may be removably positioned within the chamber of the housing such that the liquid container is accessible through the insertion window. Such position of the liquid container allows easy access and replacement of the liquid container.

As used herein, the term "liquid container" refers to an article comprising an aerosol-generating substrate or aerosol-forming substrate that is capable of releasing volatile compounds that can form an aerosol. This may take place when the substrate is heated or atomized. The substrate, when heated, may release volatile compounds that can form an aerosol. The liquid container may be also referred to as cartridge. In the following text, the terms liquid container and cartridge will be used interchangeably. The cartridge is preferably removably couplable to an aerosol-generating device. As used herein, the term 'removably couplable' is used to mean that two or more components of the system, such as the cartridge and the device, can be coupled and uncoupled from one another without significantly damaging either component. For example, the cartridge may be removed from the device when the aerosol-forming substrate has been consumed. The cartridge may be disposable. The cartridge may be reusable.

The terms "retention means", "retention mechanism" and "retention system" may be used interchangeably throughout this text.

As used herein, the term "aerosol-generating device" is a device that engages or interacts with a liquid container comprising an aerosol-forming substrate to form an inhalable aerosol. The device interacts with the aerosol-forming substrate to generate an aerosol.

The aerosol-generating device may be an electrically operated aerosol-generating device comprising a heating means that is operated by electrical power to heat an aerosol-forming substrate of a cartridge to generate an aerosol. The heating means may be a heater comprising one or more heating elements for heating air supplied to an aerosol-forming substrate. The heating means may be a heater comprising one or more heating elements for heating the aerosol-forming substrate. The heating means may be an inductor for heating a susceptor, for example to heat air supplied to an aerosol-forming substrate or to heat the substrate.

The heating element may be replaced by other atomizing means. For example, the substrate may be atomized using a vibrating element, such as a vibrating diaphragm or a vibrating mesh.

As used herein, the term "chamber" refers to a hollow cavity defined within the housing into which the cartridge may be inserted. The cartridge may be positioned transverse to the longitudinal axis of the housing. The chamber may be elongated, positioned along the longitudinal axis of the housing. The chamber may be positioned adjacent or proximal to the mouthpiece end of the housing. The chamber may be positioned adjacent or proximal to the distal end of the housing. The chamber may be positioned in the middle between the mouthpiece end and the distal end of the housing.

The chamber may comprise a mouthpiece end, a distal end, and a sidewall positioned therebetween. The mouthpiece end of the chamber is positioned adjacent, towards or facing the mouthpiece end of the device. The distal end is positioned adjacent, towards or facing the distal end of the device. The sidewall forms an inner periphery of the chamber and defines a cavity into which the cartridge is inserted. The cartridge comprises a mouthpiece end and a distal end. The mouthpiece end and the distal end of the cartridge correspond to the mouthpiece end and the distal end of the device. When the cartridge is positioned inside the chamber, the mouthpiece end of the cartridge is positioned adjacent the mouthpiece end of the chamber The cartridge and the chamber may be structured such that the structure of the cartridge complements the structure of the chamber. For example, the chamber may be asymmetric. The cartridge may be also asymmetric, copying the shape of the chamber. For example, the cartridge may be tapered towards its mouthpiece end; the chamber may be also tapered towards its mouthpiece end. This may help in preventing improper loading of the cartridge in the chamber.

The cartridge may be provided with one or more heating elements and one or more electrical connection portions. One or more of the electrical connection portions may extend beyond an external surface of the liquid container. The electrical connection portion may connect to a cartridge electrical connector when the cartridge is positioned in the chamber. In other words, where the heating element forms part of the cartridge, the cartridge may further comprise one or more electrical contacts by which the heating element is connectable to a power supply, for example a power supply in the aerosol-generating device.

The device may comprise control circuitry for controlling a supply of power from the power supply to the heating element. The control circuitry may comprise one or more microprocessors or microcontrollers. The device may comprise a cartridge electrical connector. The control circuitry may be in electrical connection with each of the power source and the cartridge electrical connector, to selectively allow supply of electric current from the power source to the cartridge electrical connector. The cartridge electrical connector may be fixedly attached to the inner periphery of the chamber (the sidewall of the chamber), such that the cartridge electrical connector is configured to connect to the electrical connection portion provided on the cartridge when the cartridge is installed in the chamber.

As used herein, the term "insertion window" refers to an opening defined in the sidewall of the housing of the aerosol-generating device, through which the cartridge can be inserted, removed, or accessed. The insertion window defines an opening in the housing through which the chamber can be accessed. The insertion window may be a cut-out in the sidewall. The insertion window may be provided in a form of multi-part split arrangement that forms the insertion window upon manual alteration.

The housing of the aerosol-generating device may be a two-piece sliding housing in which the insertion window is opened by pulling the two pieces of the housing apart. In this embodiment, the housing includes a first sliding member, a second sliding member, and a connecting member. The first sliding member includes a first attachment end. The second sliding member includes a second attachment end. In a closed (retracted) state, the insertion window is closed and the cartridge or the chamber is not accessible. In the closed state, the first attachment end of the first sliding member is attached to the second attachment end of the second sliding member. The connecting member in this embodiment may be a curved section with an opening. The connecting member may be coaxially positioned and slideably attached to at least a portion of each of the first sliding member and the second sliding member. The first sliding member and the second sliding member are configured to be detached and linearly moved away from each other. When the first sliding member and the second sliding member are moved away from each other, they may slide relative to the connecting member. Such movement of the first sliding member and the second sliding member may expose an insertion window, through which the cartridge may be inserted or removed. The insertion window then facilitates access to the chamber.

The aerosol-generating device may comprise a mouthpiece. The aerosol-generating device may be formed as a single unit including the mouthpiece. The aerosol-generating device and the mouthpiece may be two separate units. The aerosol-generating device and the mouthpiece may be threadably engaged or snap-fitted together.

The cartridge may be provided in a form of an elongated body having a mouthpiece end and a distal end and defining a sidewall therebetween. Once the cartridge is positioned in the chamber, the mouthpiece end and the distal end of the cartridge may be positioned adjacent to the mouthpiece end and the distal end of the device, respectively.

The cartridge may be cylindrical. The cartridge may be cuboid, triangular-prism-shaped or parallelepiped-shaped. The cartridge may be of any suitable shape. The shape of the cartridge may correspond to the shape of the chamber.

The liquid container may comprise a liquid transfer mechanism. The liquid transfer mechanism may be made from a porous soaking material. The liquid transfer mechanism may transfer the liquid from the liquid container towards the heater.

The heater comprises one or more heating elements. In this description reference to a heating element means one or more heating elements.

The heating element may form part of the cartridge, part of a heat diffuser provided close to or around the cartridge in order to heat the cartridge more uniformly, part of the aerosol-generating device, or any combination thereof. The heating element may form part of the cartridge.

The heating element may be shaped as a needle, pin, rod, or blade that may be inserted into the cartridge. The aerosol-generating device may comprise more than one type of heating element.

The heating element may comprise one or more external heating elements, one or more internal heating elements, or one or more external heating elements and one or more internal heating elements. As used herein, the term "external heating element" refers to a heating element that is positioned outside of the cartridge when an aerosol-generating system comprising the cartridge is assembled. As used herein, the term "internal heating element" refers to a heating element that is positioned at least partially within the cartridge when an aerosol-generating system comprising the cartridge is assembled. The heating element may be embedded in the cartridge.

The heating element may be an electrically resistive heating element. The heating element may comprise a susceptor in thermal contact with the cartridge. The heating element may be a susceptor forming part of the cartridge. Preferably, the susceptor is embedded in the cartridge.

As used herein, the term 'susceptor' refers to a material that can convert electromagnetic energy into heat. When located within a fluctuating electromagnetic field, eddy currents induced in the susceptor cause heating of the susceptor. As the susceptor is in thermal contact with the cartridge, the cartridge is heated by the susceptor.

In such embodiments, the cartridge is designed to engage with an electrically-operated aerosol-generating device comprising an induction heating source. The induction heating source, or inductor, generates the fluctuating electromagnetic field for heating a susceptor located within the fluctuating electromagnetic field. In use, the cartridge engages with the aerosol-generating device such that the susceptor is located within the fluctuating electromagnetic field generated by the inductor.

The cartridge may contain a single susceptor. The cartridge may comprise more than one susceptor.

The heating element may be a coil-type heating element. The coil-type heating element may be positioned coaxially within the liquid container. The coil-type heating element may be positioned within the cartridge, adjacent to the liquid container. The heating element may be a mesh-type heating element. The mesh-type heating element may be positioned at one end of the container. The mesh-type heating element may be positioned at a sidewall of the container. More than one mesh-type heating element may be provided. The mesh-type heating elements may be positioned at one end of the container, at a sidewall of the container, or in combination of these locations.

The one or more heating elements may be provided on the mouthpiece end of the cartridge, on the distal end of the cartridge, on the sidewall of the cartridge, or in any combination of these locations. The heating elements may be provided in multiple locations. Once the cartridge is positioned within the chamber, the one or more heating elements may be positioned such that they are in direct or indirect contact with the power source. The power source is then able to supply power or energy to heat the heating elements. The heating elements then are able to heat the cartridge or the substrate positioned therein to generate the aerosol.

The aerosol-forming substrate comprises a liquid aerosol-forming substrate. The liquid aerosol-forming substrate may comprise a nicotine solution. The liquid aerosol-forming substrate preferably comprises a tobacco-containing material comprising volatile tobacco flavour compounds which are released from the liquid upon heating. The liquid aerosol-forming substrate may comprise a non-tobacco material. The liquid aerosol-forming substrate may include water, solvents, ethanol, plant extracts and natural or artificial flavours. Preferably, the liquid aerosol-forming substrate further comprises an aerosol former.

The aerosol-forming substrate may comprise both solid and liquid components. The aerosol-forming substrate may comprise tobacco. The aerosol-forming substrate may comprise a tobacco-containing material containing volatile tobacco flavour compounds which are released from the substrate upon heating. The aerosol-forming substrate may comprise a non-tobacco material. The aerosol-forming substrate may comprise tobacco-containing material and non-tobacco containing material.

The aerosol-forming substrate may include at least one aerosol former. As used herein, the term 'aerosol former' is used to describe any suitable known compound or mixture of compounds that, in use, facilitates formation of an aerosol. Suitable aerosol formers are substantially resistant to thermal degradation at the operating temperature of the aerosol-generating article. Examples of suitable aerosol formers are glycerine and propylene glycol. The aerosol-forming substrate may comprise a single aerosol former. The aerosol-forming substrate may comprise a combination of two or more aerosol formers.

The aerosol-generating article may comprise a liquid aerosol-forming substrate and a liquid retention medium for retaining the liquid aerosol-forming substrate.

The liquid retention medium may comprise an absorbent material, for example an absorbent polymeric material. Examples of suitable liquid retention materials include fibrous polymers and porous polymers such as open-cell foams. The liquid retention medium may comprise a fibrous cellulose acetate or a fibrous cellulose polymer. The liquid retention medium may comprise a porous polypropylene material. Suitable materials capable of retaining a liquid will be known to the skilled person.

The liquid retention medium is either located within an air-flow path through the cartridge or defines at least a portion of an air-flow path through the cartridge. Preferably, one or more holes defined through the liquid retention medium define a portion of the air-flow path through the cartridge between the distal end of the cartridge and the mouth end of the cartridge.

The liquid retention medium may be in the form of a tube having a central lumen. Walls of the tube would then be formed from, or comprise, a suitable liquid-retention material.

The housing may comprise retention means adapted to retain the cartridge within the housing. The retention means may be positioned within the chamber. The retention means may be positioned within the chamber, adjacent the distal end of the housing. The retention means may be positioned within the chamber, adjacent the mouthpiece end of the housing. The retention means may be positioned within the chamber, adjacent the sidewall of the housing. The retention means may be positioned within the chamber opposite the insertion window.

The retention means may be an axial push-type retention system. The retention system may include axial biasing means (i.e. biasing means which generate biasing force along the longitudinal axis of the device). The retention system may comprise at least one axial elastic element. The axial elastic element may be an axial spring. The retention system may comprise two axial springs. The retention system may comprise more than two axial springs, for example three, four or five axial springs. The springs may be made of metal. The axial biasing means may be provided adjacent the mouthpiece end of the chamber, adjacent the distal end of the chamber, or at both these locations.

The axial biasing means may be coupled to a force distribution member, which ensures that the biasing force generated by the axial biasing means is evenly distributed across at least part of the mouthpiece end of the cartridge, the distal end of the cartridge, or both ends of the cartridge, as appropriate. The axial biasing means and the force distribution member may be positioned such that the axial biasing means facilitate a biasing action along the longitudinal axis of the device. The force distribution member may be a plate, positioned at the free end of the biasing means, facing the inside space of the chamber.

The axial push-type retention system may comprise two axial springs mounted on the distal end of the housing, and a plate attached to free ends of the axial springs. The axial springs and the plate may be positioned such that the axial springs facilitate a spring action along the longitudinal axis of the device.

The cartridge may be installed as follows. A first end portion (e.g. the distal end) of the cartridge is initially pushed through the insertion window of the chamber. Once the first end portion is entirely positioned within the chamber and contacts the biasing means and/or the force distribution member, the cartridge is pushed axially against the biasing means. The biasing means is biased towards a first end (e.g. towards the distal end) of the chamber such that the second end portion (e.g. the mouthpiece end) of the cartridge can enter the chamber and may be positioned within the chamber. The cartridge is pushed all the way down inside the chamber, so that the biasing means force the cartridge towards the opposite end (e.g. the mouthpiece end) of the chamber. In an embodiment where the chamber comprises a heater adjacent the end of the chamber, the cartridge is brought into contact with the heater. In an embodiment where the cartridge is provided with a heater and an electrical connection portion at the second end of the cartridge, an electrical contact between the electrical connection portion and the cartridge electrical connector of the chamber is continuously maintained by the biasing force of the biasing means.

The cartridge may be uninstalled as follows. The second end portion is manually accessed through the insertion window. The second end portion is pulled out of the chamber. Biasing action of the biasing means causes uninstallation of the cartridge from the chamber.

The retention means may be a radial push-type retention system. The retention system may include radial biasing means (i.e. biasing means which generate biasing force transverse to the longitudinal axis of the device). The retention system may comprise at least one radial elastic element. The radial elastic element may be a radial spring. The retention system may comprise two radial springs. The retention system may comprise more than two radial springs, for example three, four or five radial springs. The springs may be made of metal. The radial biasing means may be provided adjacent the sidewall in the interior of the chamber. The radial biasing means may be provided opposite the insertion window.

The radial biasing means may be coupled to a force distribution member, which ensures that the biasing force generated by the axial biasing means is evenly distributed across at least part of the sidewall of the cartridge. The radial biasing means and the force distribution member may be positioned such that the axial biasing means facilitate a biasing action transverse to longitudinal axis of the device. The force distribution member may be a plate, positioned at the free end of the biasing means, facing the inside space of the chamber.

The radial push-type retention system may further comprise retaining means. The retaining means may be for example based on the principle of snap-fitting, press-fitting or interference fitting. The retaining means may comprise one or more retention levers. For example, two retention levers may be provided. The or each of the retention levers may include a first end and a second end. The second end of each retention lever is mounted on the inner periphery of the housing. When no cartridge is mounted in the chamber, the first end may be free. The first end of the retention levers may be provided with retention features such as hooks, protrusions or loops. The second end may be mounted on the inner periphery of the housing using mounting means which allow the retention levers to rotate. For example, the mounting means may be torsion springs.

The radial push-type retention system may further comprise ejection means. The ejection arrangement may include an actuator and pushing means. For example, the actuator may be a spring-type actuation switch. For example, the pushing means may be one or more (e.g. two) push pins. The actuator may be positioned on an external surface of the housing. The or each pushing means may extend through the housing such that the pushing means contact and actuate the cartridge, the retention means, or both.

The radial push-type retention system may comprise two radial springs mounted on the distal end of the housing, and a plate attached to free ends of the radial springs. The radial springs and the plate may be positioned such that the radial springs facilitate a spring action transverse to the longitudinal axis of the device. The housing may further comprise two retention levers, a pair of push pins and an actuation switch. The push pins may extend through the housing and contact each retention lever. Upon pressing the actuation switch, the push pins push the retention levers. Such push of the retention levers facilitates pivotal movement of the retention levers and therefore may release the cartridge.

The external surface of a cartridge or a liquid container for use with the radial push-type retention system may comprise retention features compatible with the retention features provided on the retention levers. For example, the cartridge may be provided with notch portions, depressions, or hooks. The number of the retention features provided on the cartridge corresponds to the number of retention levers and/or the number of the retention features provided on the retention levers. There may be two retention levers, each one provided with a hook, and two notch portions provided on the cartridge.

The cartridge may be installed as follows. The cartridge is pushed radially through the insertion window in the chamber. As the cartridge is pushed in the chamber, the cartridge contacts the plate. The cartridge is further pushed to compress the radial springs, such that the first end of each retention lever engages with the notch portions of the cartridge. Such arrangement of the cartridge with the retention levers retains the cartridge within the chamber of the housing.

The cartridge may be uninstalled as follows. The actuation switch is pushed. Pushing of the actuation switch causes the retention levers to pivot, which causes removal of the first ends of the retention levers from the notch portions of the cartridge. The radial springs then push the support plate, which pushes the cartridge radially. Such radial push causes removal of to the cartridge from the chamber of the housing.

The cartridge may be snap-fitted into the chamber.

The retention means may comprise a door unit. The door unit is adapted to cover the insertion window to allow or restrict the access to the chamber and/or the cartridge through the sidewall of the housing. The aerosol-generating device may include a mouthpiece, a cartridge, a retention mechanism and a door unit. The door unit may be provided with embodiments in which the insertion window is formed as a cut-out.

The door unit may be a pivot-type door that pivots about a pivot axis. The door unit may be provided with hinges which define the pivot axis. The door unit may be pivotally attached proximal to the insertion window of the housing.

The door unit may be a sliding door that slides along the external surface of the housing. The door unit may be attached to the housing, proximal to the insertion window of the housing. The door unit may slide along the longitudinal axis of the housing in order to allow or restrict an access to the cartridge through the insertion window.

The door unit may be a pull-apart type door that may be pulled apart from the housing. The door unit may be for example snap-fitted to the housing. When the door unit is to be opened, the user may pull the door unit out and away from the chamber to release the door unit. The insertion window may thus be made accessible. When the door unit is to be closed, the pull apart door is pushed through the insertion window to snap-fit with the housing.

In case the door unit is not provided, the sidewall of the cartridge may be configured such that when the cartridge is inserted into the chamber, the sidewall of the cartridge is levelled with the sidewall of the housing and the chamber is thus closed by the sidewall of the cartridge.

The retention mechanism may be a push-type ejection arrangement. A push-type ejection arrangement retains the cartridge within the chamber once the cartridge is pushed through the insertion window A push-type ejection arrangement ejects the cartridge from the chamber once the cartridge is pushed for a second time through the insertion window.

The retention mechanism may be a magnetic retention mechanism. A magnetic retention mechanism magnetically retains the cartridge within the chamber until a sufficiently high pulling force is applied to the cartridge for removal.

The aerosol-generating device may further also include a sliding mechanism. The sliding mechanism may include at least one slide channel. The slide channels may facilitate easier entry and exit of the cartridge in the chamber through the insertion window.

The retention means of the aerosol-generating device may comprise any combination of different elements of the radial push-type and axial push-type retention systems described above. The retention means may comprise a magnetic retention mechanism as described above, in addition to the axial push-type retention system described above. The retention means may comprise a magnetic retention mechanism as described above, in addition to the radial push-type retention system described above. The retention means may comprise a magnetic retention mechanism as described above, in addition to any combination of different elements of the radial push-type and axial push-type retention systems described above. The retention means may comprise any combination of elements from the retention systems or mechanisms described above, in addition to one or more retention levers.

Preferably, the aerosol-generating device is a portable or handheld aerosol-generating device that is comfortable for a user to hold between the fingers of a single hand. The aerosol-generating device may be a personal vaporizer. The aerosol-generating device may be substantially cylindrical in shape. The aerosol-generating device may have a length of between approximately 70 millimetres and approximately 120 millimetres.

The device may comprise a power supply for supplying electrical power to the heating element. The power supply may be any suitable power supply, for example a DC voltage source such as a battery. The power supply may be a Lithium-ion battery. The power supply may be a Nickel-metal hydride battery, a Nickel cadmium battery, or a Lithium based battery, for example a Lithium-Cobalt, a Lithium-Iron-Phosphate, Lithium Titanate or a Lithium-Polymer battery.

As used herein, the terms 'upstream' and 'downstream' are used to describe the relative positions of elements, or portions of elements, of the heat diffuser, aerosol-generating article, or aerosol-generating device, in relation to the direction in which air is drawn through the system during use thereof.

As used herein, the term 'longitudinal' is used to describe the direction between the upstream end and the downstream end of the heat diffuser, aerosol-generating article, or aerosol-generating device and the term 'transverse' is used to describe the direction perpendicular to the longitudinal direction.

Figure 1:
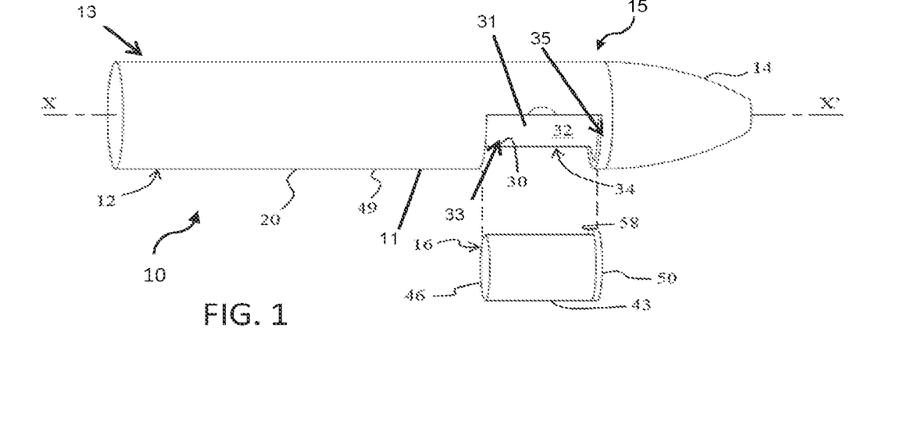
FIG. 1 is an overall view of an aerosol-generating system with a liquid container removed from an aerosol-generating device according to one embodiment of the invention.

The aerosol-generating system 10 comprises an aerosol-generating device 12, a mouthpiece 14, and a cartridge 16. The exemplary aerosol-generating device 12 comprises a housing 20, a retention mechanism 18 (see FIG. 6), and a door unit 21. The aerosol-generating device 12 and the mouthpiece 14 may be formed together as a single elongated unit. The aerosol-generating device 12 and the mouthpiece 14 may be formed as separate units. In such case, the mouthpiece 14 threadably engages with the housing 20 of the aerosol-generating device 12.

In the following text, an embodiment will be described where the aerosol-generating device 12 and the mouthpiece 14 are formed as separate units. The principles explained in the text are equally applicable to the embodiment in which the mouthpiece is integral with the housing.

Figures 2, 3:
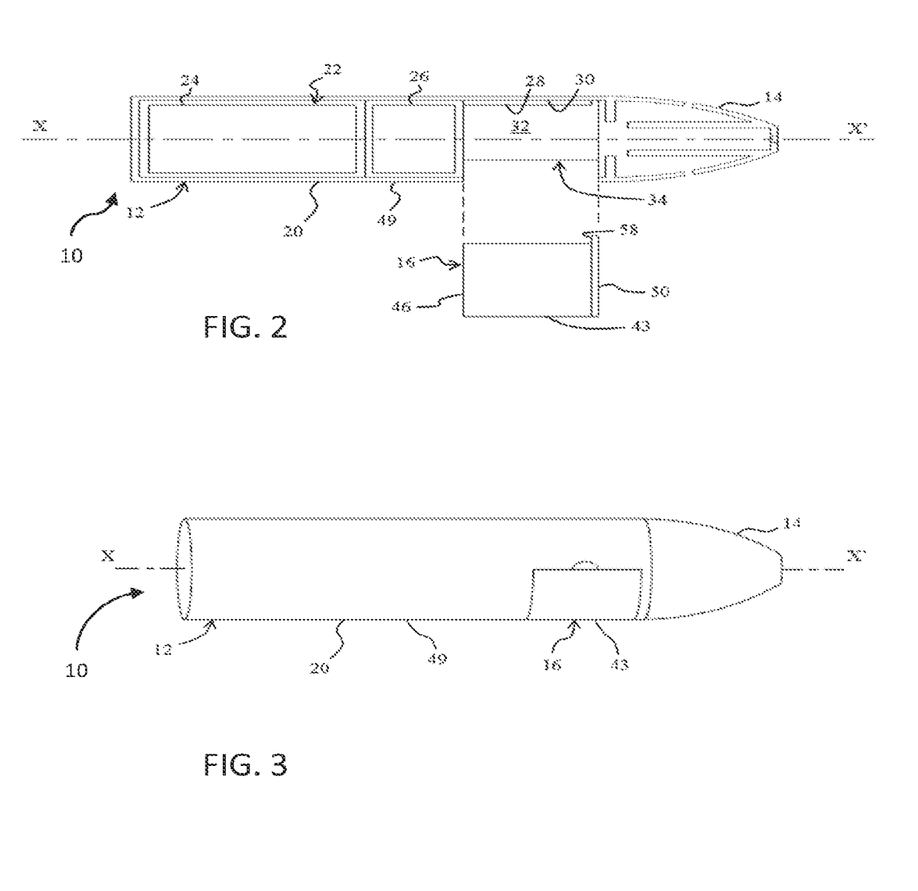
FIG. 2 is a cross section of the aerosol-generating system from FIG. 1.
FIG. 3 is an overall view of an aerosol-generating system from FIG. 1 with a liquid container inserted into an aerosol-generating device.

The housing 20 of the aerosol-generating device 12 extends along a longitudinal axis X-X'. The housing 20 comprises a chamber 32 into which the cartridge 16 is received. The chamber 32 is proximal to a mouthpiece end of the housing 20. The housing 20 defines a mouthpiece end 15, a distal end 13, and a sidewall 11 between the mouthpiece end 15 and the distal end 13. The chamber 32 is defined within an interior of the housing 20. The housing 20 comprises an insertion window 34, which allows access to the chamber 32.

The housing 20 comprises the cartridge chamber 32 and electrical components 22. The housing 20 supports and mounts the electrical components 22. The electrical components 22 include a power source 24 (for example a lithium battery), a control circuitry 26, and a cartridge electrical connector 28. The control circuitry 26 is in electrical connection with each of the power source 24 and the cartridge electrical connector 28. The control circuitry 26 selectively allows supply of electric current from the power source 24 to the cartridge electrical connector 28. The cartridge electrical connector 28 is attached to an inner periphery 30 of the chamber 32. The cartridge electrical connector 28 connects the cartridge 16 to the power source 24 and to the control circuitry 26 when the cartridge is installed in the chamber 32. The cartridge electrical connector 28 facilitates supply of electric current to the cartridge 16.

In an exemplary embodiment, the cartridge 16 comprises a liquid container 46, a heater comprising a heating element 48, and a liquid transfer mechanism 50. In this exemplary embodiment, the heating element 48 is a mesh-type heating element (see FIG. 4). The heating element 48 is positioned at one end of the liquid container 46. The liquid transfer mechanism 50 contacts the heating element 48.

Figure 4:
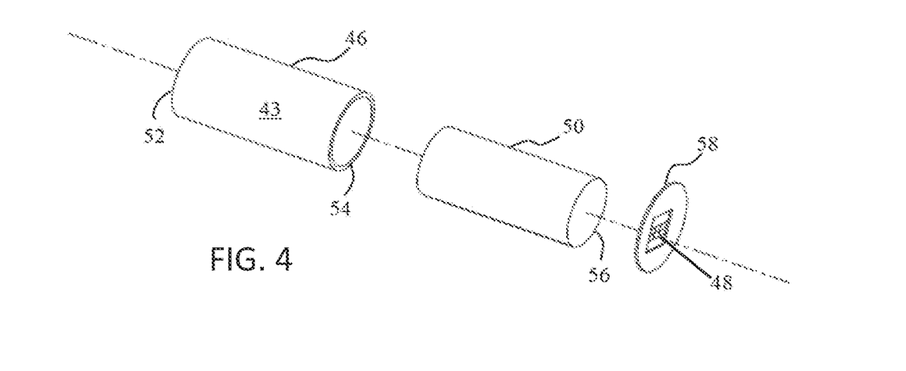
FIG. 4 is an exploded view of a liquid container.

The below described example of the cartridge 16 comprises a liquid container 46, a heating element 48, and a liquid transfer mechanism 50. In this exemplary embodiment, the heating element 48 is a mesh-type heating element. Such a cartridge is shown in FIG. 4. The principles explained in the text are equally applicable to the embodiment in which the cartridge comprises a coil-type heating element, or any other atomizing element known in the art.

The cartridge 16 may be for example of the type described in WO2016/174179. The liquid container 46 is a cylindrical liquid storage medium that stores and carries e-liquid. The liquid container 46 contains the liquid transfer mechanism 50. The liquid container 46 has a closed end 52 and an open end 54. The liquid transfer mechanism 50 is made of a porous soaking material. The liquid transfer mechanism 50 includes a liquid transfer end 56. The liquid transfer mechanism 50 is coaxially positioned within the liquid container 46, such that the liquid transfer end 56 abuts with the open end 54 of the liquid container 46. The liquid transfer mechanism 50 transfers the liquid from the liquid container 46 to the heating element 48, where the liquid is subsequently vaporized.

The heating element 48 is a flat mesh-type heater unit disposed on the open end 54 of the liquid container 46. The heating element 48 seals the open end 54 of the liquid container 46. At least one electrical connection portion 58 of the heating element 48 extends beyond an external surface 43 of the liquid container 46, such that the electrical connection portion 58 connects to the cartridge electrical connector 28 when the cartridge 16 is positioned in the cartridge chamber 32 of the aerosol-generating device 12.

The housing 20 of the aerosol-generating device 12 forms the insertion window 34, through which the cartridge 16, the chamber 32, or both are accessible. The insertion window 34 may be formed as a cut-out in the housing 20 of the aerosol-generating device (see, e.g. FIG. 1). The insertion window 34 facilitates access to the cartridge chamber 32 of the housing 20 of the aerosol-forming device 12.

Figure 5:
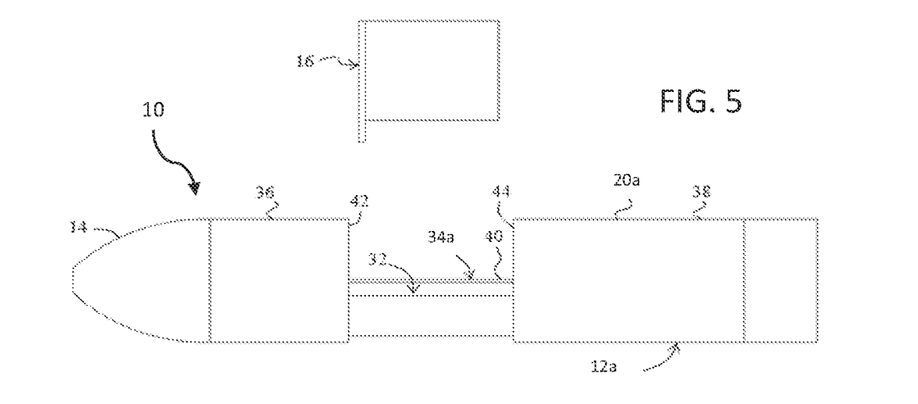
FIG. 5 is an overall view an aerosol-generating system with a liquid container removed from an aerosol-generating device according to another embodiment of the invention.

The insertion window 34a may be formed as a multi-part split arrangement. An aerosol-generating device 12a with an insertion window 34a formed as a multi-part split arrangement is shown in FIG. 5. The insertion window 34a opens upon manual alteration of the housing 20a. The housing 20a includes a first sliding member 36, a second sliding member 38, and a connecting member 40. The first sliding member 36 and the second sliding member 38 include a first attachment end 42 and a second attachment end 44, respectively. The first attachment end 42 of the first sliding member 36 is in snap fit attachment to the second attachment end 44 of the second sliding member 38. The connecting member 40 is a substantially curved section with an opening. The connecting member 40 is coaxially positioned and slideably attached to at least a portion of each of the first sliding member 36 and the second sliding member 38. The first sliding member 36 and the second sliding member 38 are detached and linearly moved away from each other, to slide relative to the connecting member 40. Such movement of the first sliding member 36 and the second sliding member 38 forms the insertion window 34a, which facilitates access to the chamber 32.

In the description below, an embodiment with a cut-out insertion window 34 is described. However, many of the principles explained in the text are equally applicable to the embodiment in which the insertion window is formed as a multi-part split arrangement.

Figure 6:
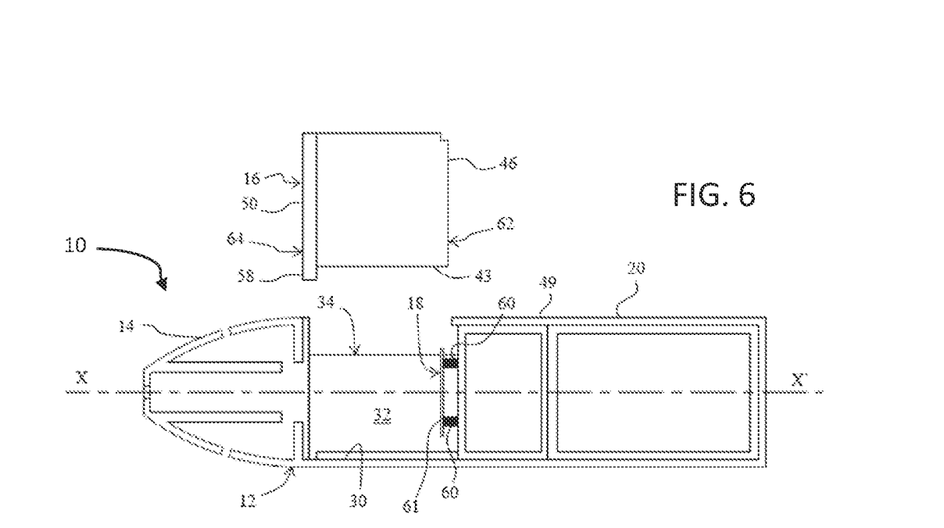
FIG. 6 is a cross sectional view of an aerosol-generating system with retention means according to one embodiment.
Figure 7:
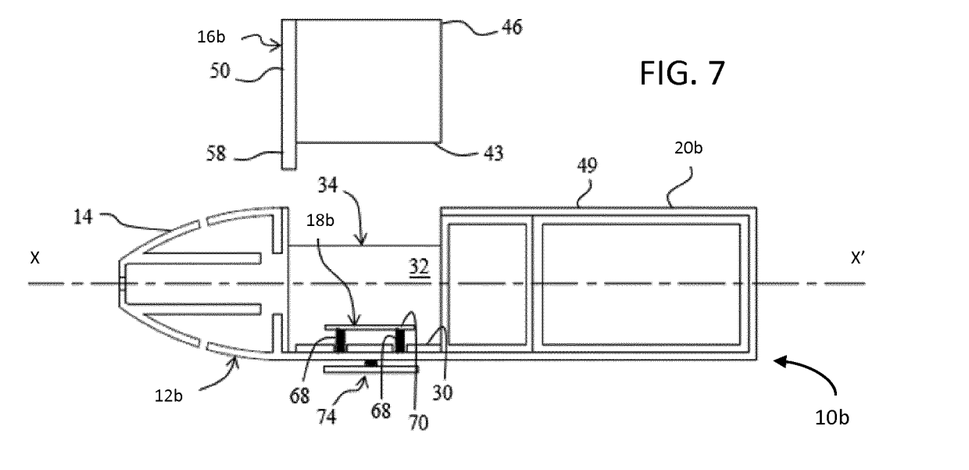
FIG. 7 is a cross sectional view of an aerosol-generating system with retention means according to another embodiment.

To retain the cartridge 16 within the chamber 32, a retention mechanism 18 is provided. The retention mechanism 18 may comprise an axial push-type retention system. The retention mechanism 18 may comprise a radial push-type retention system 18b. The structure and arrangement of the cartridge 16 may vary for each type of the retention mechanism 18.

An exemplary axial push-type retention system comprises two axial springs 60 and a bottom plate 61. The axial spring 60 is attached to the housing 20, within the chamber 32. The bottom plate 61 is attached to the free ends of the axial springs 60. The axial springs 60 and the bottom plate 61 are positioned such that the axial springs 60 facilitate a spring action along the longitudinal axis X-X' of the aerosol-generating device 12. The axial springs 60 and the bottom plate 61 are positioned at the distal end 33 of the chamber 32.

In order to install the cartridge 16 in the chamber 32, a distal end portion 62 of the cartridge 16 is initially pushed through the insertion window 34 and into the chamber 32 such that the distal end portion 62 is entirely positioned within the chamber 32. The distal end portion 62 contacts the bottom plate 61. The cartridge 16 is then pushed axially against the bottom plate 61. The mouthpiece end portion 64 enters the chamber 32 and is positioned within the chamber 32. The mouthpiece end portion 64 is positioned within the chamber 32. An external surface 43 of the cartridge 16 abuts an external surface 49 of the housing 20. The electrical contact between the electrical connection portion 58 and the cartridge electrical connector 28 is established and maintained.

In other words, in order to install the cartridge 16 to the aerosol-generating device 12, the cartridge 16 is initially pushed through the insertion window 34 of the aerosol-generating device 12. The cartridge 16 enters the chamber 32. The cartridge 16 is then further pushed to slide through the chamber 32 and actuate the springs 60. The electrical connection portion 58 of the heating element 48 positioned on the cartridge 16 contacts the cartridge electrical connector 28 positioned in the chamber 32 of the housing 20.

In order to uninstall the cartridge 16 from the chamber 32, the mouthpiece end portion 64 of the cartridge 16 is manually accessed through an access slot and is pulled out of the chamber 32. Spring action of the axial spring 60 via the bottom plate 61 causes uninstallation of the cartridge 16 from the chamber 32.

Figure 8:
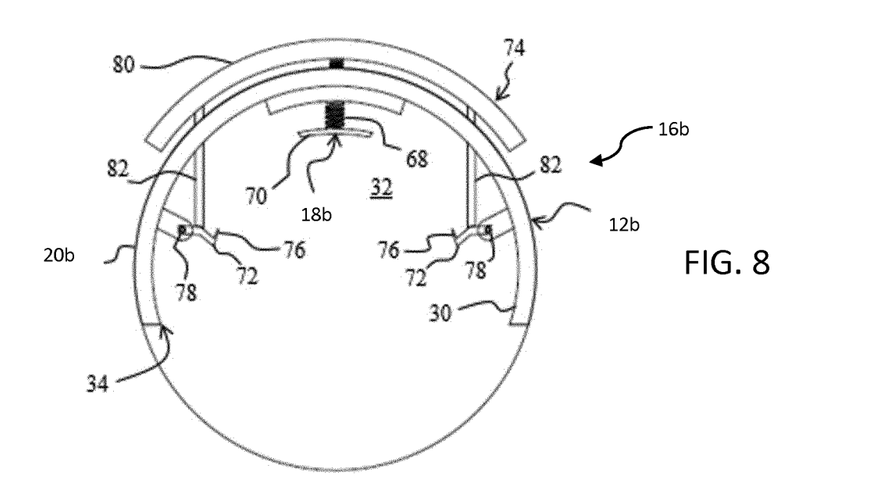
FIG. 8 is a transversal cross-sectional view of the aerosol-generating device from FIG. 7.

An exemplary radial push-type retention system 18b comprises two radial springs 68, a support plate 70, two retention levers 72, and an ejection arrangement 74. The radial springs 68 are attached to the inner periphery 30 of the housing 20b, opposite to the insertion window 34. To avoid contact of the radial springs 68 with the cartridge electrical connector 28, the radial springs 68 are positioned within spaced holes in the cartridge electrical connector 28. Spaced hole in this context means a hole which is configured to leave a gap between the inner periphery of the hole and the radial springs 68. In this way, supply of electric current to the cartridge electrical connector 28 is not disrupted. The support plate 70 is attached to the free ends of the radial springs 68.

Each of the retention levers 72 includes a first end 76 and a second end 78. The second end 78 of each retention lever 72 is mounted on the inner periphery 30 of the housing 20b. The retention levers 72 are mounted to the housing 20 via torsion springs (not shown).

The ejection arrangement 74 includes a spring-type actuation switch 80 and two push pins 82. The actuation switch 80 is positioned on an external surface 49 of the housing 20b of the aerosol-generating device 12b. Each push pin 82 extends through the housing 20b to contact each retention lever 72. Upon pressing the actuation switch 80, the push pins 82 push the retention levers 72. Such push of the retention levers 72 facilitates pivotal movement of the retention levers 72. This is in order to disengage the retention levers 72 from notch portions 84 of the cartridge 16b (described below).

Figure 9:
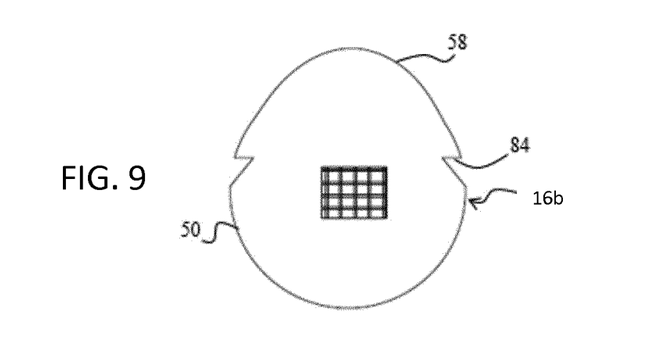
FIG. 9 is a top view of a liquid container for use with retention means from FIG. 7 and FIG. 8.

The cartridge used with the radial push-type retention system comprises two notch portions 84. The notch portions 84 are adapted to cooperate with the retention levers 72 to retain the cartridge 16b in the chamber 32.

In order to install the cartridge 16b in the chamber 32, the cartridge 16b is pushed radially (i.e., in a direction transversal to the longitudinal axis X-X' of the aerosol-generating device 12b) through the insertion window 34. As the cartridge 16b is pushed inside the chamber 32, the cartridge 16b contacts the support plate 70. The cartridge 16b is further pushed to compress the radial springs 68, such that the first end 76 of each retention lever 72 engages with the notch portions 84 of the cartridge 16b. Such arrangement of the cartridge 16b with the retention levers 72 retains the cartridge 16b within the chamber 32.

In order to uninstall the cartridge 16b from the chamber 32, the actuation switch 80 is pushed. Such push of the actuation switch 80 causes the retention levers 72 to pivot, which causes removal of the first ends 76 of the retention levers 72 from the notch portions 84 of the cartridge 16b. The radial springs 68 then push the support plate 70, which pushes the cartridge 16b radially. Such radial push causes removal of to the cartridge 16b from the chamber 32.

In some exemplary embodiments, door unit 21 is provided to cover/uncover the insertion window 34 of the housing 20 and to restrict/allow the access to the cartridge 16. A door unit 21 may be provided with any housing 20 in which the insertion window 34 is formed as a cut-out.

Figure 10:
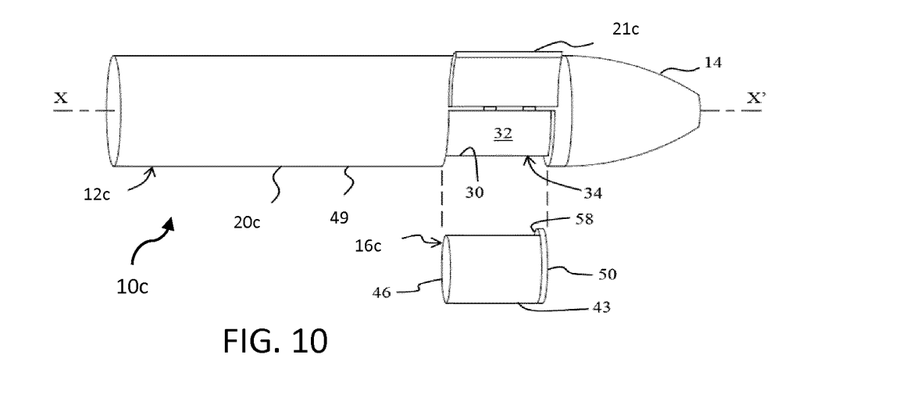
FIG. 10 is a side view of an aerosol-generating device with a door unit according to one embodiment.

The door unit 21 may be a pivot-type door that pivots about a pivot axis (see FIG. 10). The door unit 21 may be a sliding door that slides along the external surface 49 of the housing 20 (see FIG. 11). The door unit 21 may be a pull-apart type door that may be pulled apart from the housing 20 (see FIG. 12).

A pivot-type door unit 21c is pivotally attached to the housing 20c, proximal to the insertion window 34. The pivot-type door unit 21c pivots about the pivot axis in order to allow/restrict an access to the cartridge 16c through the insertion window 34 of the housing 20c.

Figure 11:
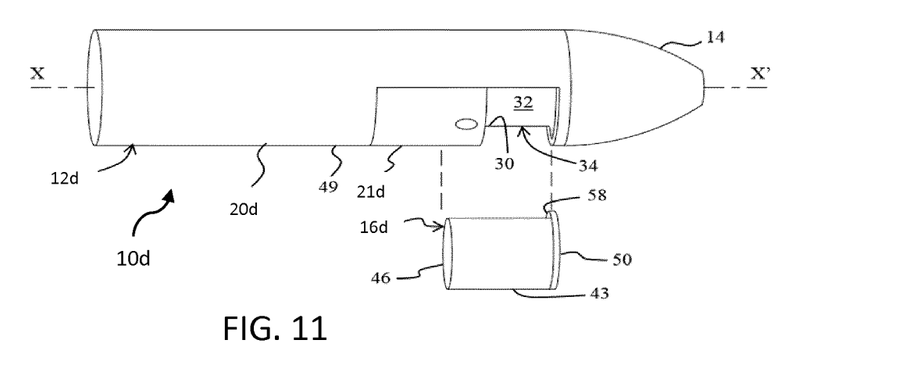
FIG. 11 is a side view of an aerosol-generating device with a door unit according to one embodiment.

A sliding door unit 21d is slideably attached to the housing 20d, proximal to the insertion window 34. The sliding door unit 21d slides along the longitudinal axis X-X' of the housing 20d in order to allow/restrict an access to the cartridge 16d through the insertion window 34 of the housing 20d.

Figure 12:
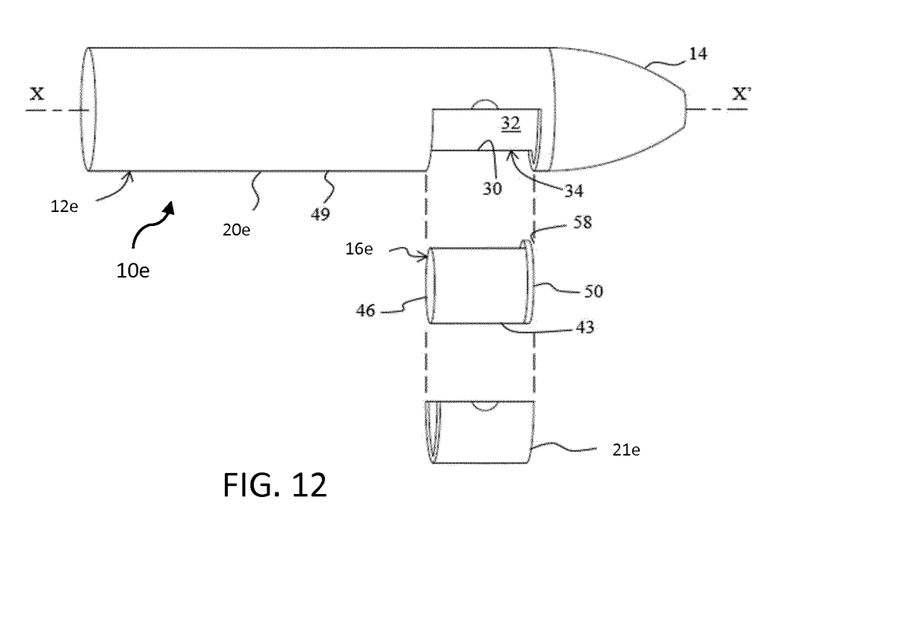
FIG. 12 is a side view of an aerosol-generating device with a door unit according to one embodiment.

A pull apart type door unit 21e is pulled out from the chamber 32 in order to allow an access to the cartridge 16e. After replacing the cartridge 16e, the pull apart door is pushed through the insertion window 34 in the chamber 32, to snap-fit with the housing 20e. This restrict the access to the cartridge 16e through the insertion window 34 of the housing 20e.

The specific embodiments and examples described above illustrate but do not limit the invention. It is to be understood that other embodiments of the invention may be made and the specific embodiments and examples described herein are not exhaustive.

The invention claimed is:

1. An aerosol-generating device, comprising:
   a housing defining a mouthpiece end, a distal end, a sidewall between the mouthpiece end and the distal end, and a chamber within the housing, the chamber being configured to receive a liquid container, wherein the housing comprises retention means, wherein the retention means is disposed within the chamber and is configured to retain the liquid container within the chamber, the retention means comprising a magnetic retention mechanism; and a power source disposed within the housing, wherein the sidewall of the housing defines an insertion window through which the liquid container is positionable inside the chamber.

2. The aerosol-generating device according to claim 1, wherein the chamber has a mouthpiece end, a distal end, and a sidewall, and wherein the retention means is disposed either adjacent the sidewall of the chamber, or at the distal end of the chamber, or both.

3. The aerosol-generating device according to claim 1, wherein the retention means further comprises an axial push-type retention system.

4. The aerosol-generating device according to claim 1, wherein the retention means further comprises a radial push-type retention system.

5. The aerosol-generating device according to claim 1, wherein the housing further includes a door unit configured to cover the insertion window.

6. The aerosol-generating device according to claim 1, wherein the housing further comprises two sliding members, which are configured to be pulled apart and thus open the insertion window.

7. An aerosol-generating system, comprising:
   the aerosol-generating device according to claim 1; and
   a liquid container comprising a liquid aerosol-forming substrate.

8. The aerosol-generating system according to claim 7, further comprising a heater configured to heat the liquid aerosol-forming substrate.

9. The aerosol-generating system according to claim 8, wherein the liquid container further comprises a liquid transfer mechanism configured to transfer the liquid towards the heater.

10. A liquid container comprising a liquid aerosol-forming substrate, the liquid container being configured to be used with an aerosol-generating device according to claim 1.

11. The liquid container according to claim 10, further comprising a heater provided as a part of the liquid container.

12. The liquid container according to claim 10, further comprising a liquid transfer mechanism configured to transfer the liquid from the liquid container towards a heater.

* * * * *